United States Patent [19]
Johnson et al.

[11] 4,018,758
[45] Apr. 19, 1977

[54] 3-AMINOMETHYLENE-6,7-DIMETHOXY-2-METHYL-4-OXO-1,2,3,4-TETRAHYDRO-1-QUINOLINE CARBOXYLIC ACID ESTERS AND INTERMEDIATES LEADING THERETO

[75] Inventors: Michael R. Johnson, Gales Ferry; Jacob J. Plattner, East Lyme, both of Conn.

[73] Assignee: Pfizer Inc., New York, N.Y.

[22] Filed: Apr. 12, 1976

[21] Appl. No.: 676,103

Related U.S. Application Data

[62] Division of Ser. No. 628,808, Nov. 4, 1975, Pat. No. 3,978,064.

[52] U.S. Cl. .................. 260/240.3; 260/240 R; 260/240.7; 260/240.8; 260/287 K; 424/258; 424/248.54; 260/247.2 B
[51] Int. Cl.$^2$ .............. C07D 401/06; C07D 413/06
[58] Field of Search ..... 260/240.3, 287 K, 247.2 B, 260/240.7, 240.8, 240 R

[56] References Cited
OTHER PUBLICATIONS
Bolger, Chem. Abstracts, 66 (1967), No. 28784.

*Primary Examiner*—Arthur P. Demers
*Attorney, Agent, or Firm*—Connolly and Hutz

[57] ABSTRACT

Racemic 3-aminomethylene-6,7-dimethoxy-2-methyl-4-oxo-1,2,3,4-tetrahydro-1-quinoline carboxylic acid, alkyl, phenyl and benzyl esters as analgesic agents, synthesized from 3-hydroxymethylene-6,7-dimethoxy-2-methyl-4-oxo-1,2,3,4-tetrahydro-1-quinoline carboxylic acid, alkyl, phenyl and benzyl esters and the dextrorotatory enantiomer 3-aminomethylene-6,7-dimethoxy-2-methyl-4-oxo-1,2,3,4-tetrahydro-1-quinoline carboxylic acid, ethyl ester, an outstanding analgesic agent.

1 Claim, No Drawings

3-AMINOMETHYLENE-6,7-DIMETHOXY-2-METHYL-4-OXO-1,2,3,4-TETRAHYDRO-1-QUINOLINE CARBOXYLIC ACID ESTERS AND INTERMEDIATES LEADING THERETO

CROSS-REFERENCE TO RELATED APPLICATION

This application is a division of application Ser. No. 628,808 filed Nov. 4, 1975, now U.S. Pat. No. 3,978,064.

BACKGROUND OF THE INVENTION

This invention relates to novel racemic 3-aminomethylene-6,7-dimethoxy-2-methyl-4-oxo-1,2,3,4-tetrahydro-1-quinoline carboxylic acid, alkyl, phenyl and benzyl esters as analgesic agents, to novel racemic 3-hydroxy-methylene-6,7-dimethoxy-2-methyl-4-oxo-1,2,3,4-tetrahydro-1-quinoline carboxylic acid, alkyl, phenyl and benzyl esters, useful intermediates leading to these analgesics and to the resolved dextrorotatory enantiomer 3-aminomethylene-6,7-dimethoxy-2-methyl-4-oxo-1,2,3,4-tetrahydro-1-quinoline carboxylic acid, ethyl ester.

SUMMARY OF THE INVENTION

A preferred group of compounds of the present invention are the racemic analgesic agents of the formula

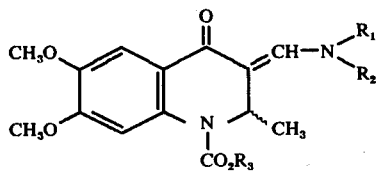

wherein $R_1$ taken separately is hydrogen or methyl; $R_2$ taken separately is hydrogen, alkyl of one to five carbon atoms, propargyl, phenyl, naphthyl, phenylalkylene wherein said alkylene has one to four carbon atoms, naphthylalkylene wherein said alkylene has from one to four carbon atoms, dimethylaminoalkylene wherein said alkylene has from two to four carbon atoms or mono-substituted 2-ethyl wherein said substituent is phenoxy or methoxhy; $R_1$ and $R_2$ when considered together with the nitrogen atoms to which they are attached form a piperidino, pyrrolidino or morpholino ring; $R_3$ is alkyl of one to five carbon atoms, phenyl, benzyl or mono-substituted phenyl or benzyl wherein the substituent is fluoro, chloro, methyl, methoxy or trifluoromethyl; and the pharmaceutically acceptable acid solution salts thereof wherein $R_2$ is said dimethylaminoalkylene.

Especially preferred within this group of compounds are those wherein $R_1$ is hydrogen and $R_3$ is alkyl of one to five carbon atoms, those wherein $R_1$ is hydrogen and $R_3$ is benzyl and those wherein $R_1$ is methyl and $R_3$ is alkyl of one to five carbon atoms.

A second preferred group of compounds, which are useful intermediates leading to the analgesic agents of the present invention, are those racemic compounds of the formula

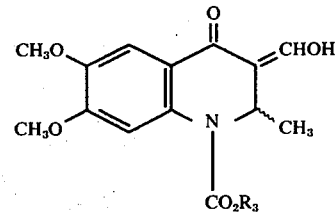

wherein $R_3$ is as previously defined.

A third preferred aspect of the present invention is the dextrorotatory enantiomer of a compound within the first preferred group of analgesic agents of the formula

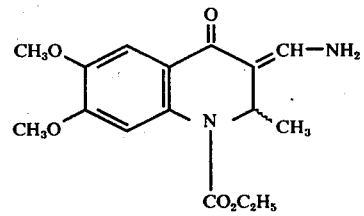

As will be recognized by one skilled in the art, the analgesic agents of the first preferred group and the useful intermediates leading to the synthesis thereof in the second preferred group possess an asymmetric carbon atom at the 2-position, and can exist in two forms. These forms can be distinguished by their ability to rotate the plane of polarized light. One form rotates the plane of polarized light to the right and is known as the dextrorotatory enantiomer or the $d(+)$ enantiomer, while the other form rotates the plane of polarized light to the left and is known as the levorotatory enantiomer or $l(-)$ enantiomer. A mixture of equal amounts of the $d$ and $l$ enantiomers of these compounds does not affect the plane of polarized light, and is known as a racemic mixture of $d\ l$ form. For the purpose of the present invention, when determining whether a compound is dextrorotatory or levorotatory, it is the effect of the compound on light having a wavelength of 5893 Angstroms, the so-called D line of sodium, which is to be considered.

Since the absolute configuration of the methyl group at the 2-position is not known the bond of the methyl substituent to the 2-position is depicted as

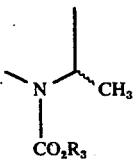

DETAILED DESCRIPTION OF THE INVENTION

In accordance with the process employed for synthesizing the compounds of the present invention, the following scheme is illustrative:

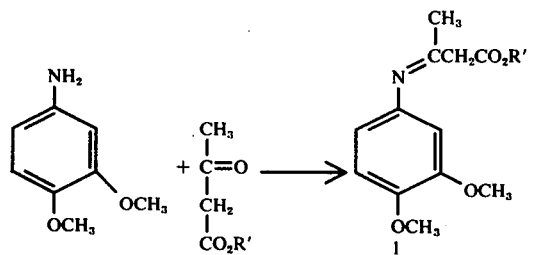
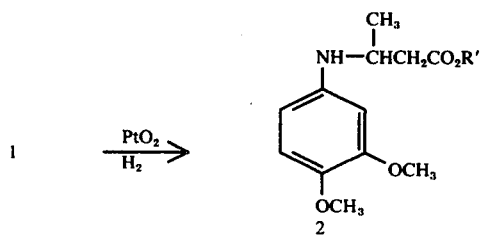
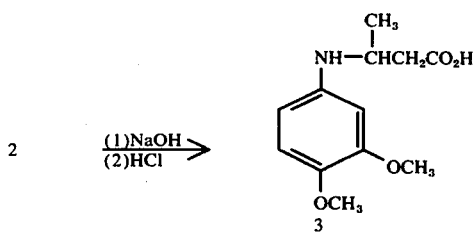
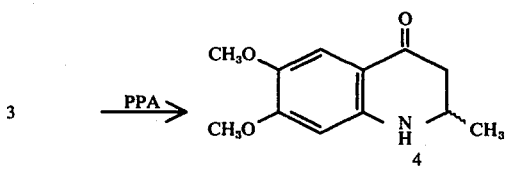
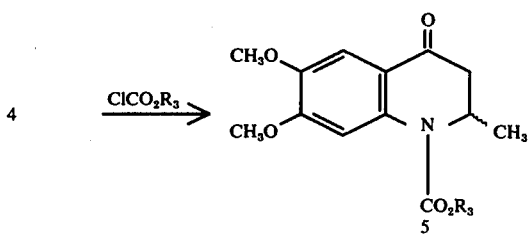
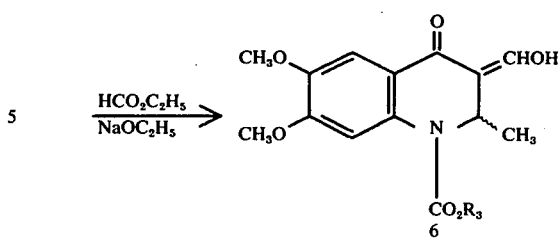

-continued

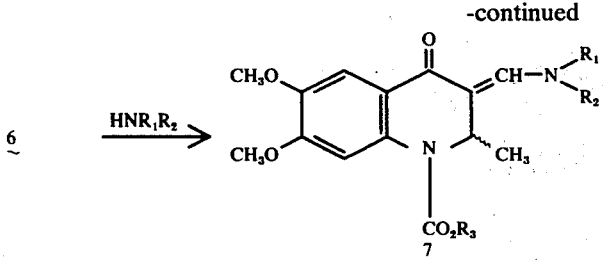

wherein $R_1$, $R_2$ and $R_3$ are previously defined, PPA represents polyphosphoric acid and R' is lower alkyl.

In the first of the above-depicted reaction steps, an alkyl acetoacetate such as ethyl acetoacetate is condensed with the appropriate 3,4-dimethoxyaniline in the presence of a suitable solvent such as benzene and a small amount of an acid catalyst such as acetic acid. Recovery of the resulting alkyl 3-[(3,4-diemthoxy)anilino]-2-butenoate (1) upon reaction completion, which may be determined by thin layer chromatography, is possible by solvent removal at reduced pressure. Recrystallization from solvents such as hexane yields the desired butenoate intermediate.

The second step of the aforesaid reaction sequence involves hydrogenation of the butenoate product of the first step utilizing conditions for the reduction of double bonds (M. Freifelder, "Practical Catalytic Hydrogenation, Techniques and Applications": Wiley-Intescience, New York, 1971), preferably catalytic hdrogenation over palladium, palladium on carbon or platinum oxide under acidic conditions, i.e., at a pH of about 3 up to 7. Acetic acid is a preferred acid for obtaining this pH. The resulting alkyl 3-[(3,4-dimethoxy)anilino]butanoate (2) may be recovered by filtration of the hydrogenated mixture, concentration under reduced pressure, dissolving resulting product in a solvent such as chloroform, washing with sodium bicarbonate solution and saturated sodium chloride, drying the organic layer using magnesium sulfate and concentration under reduced pressure.

The third step of the process involves alkaline hydrolysis of the product of the second step, employing aqueous sodium or potassium hydroxide together with a water-miscible solvent such as methanol. The resulting 3-[(3,4-dimethoxy)anilino]butanoic acid (3) containing reaction mixture may then be cooled, concentrated under reduced presure, diluted with water, neutralized with acid and extracted with an agent as chloroform. The combined organic extracts are then dried, for example using anhydrous magnesium sulfate, and concentrated under reduced pressure to give a product suitable for use in the next step of the process without further purification.

The product of the third reaction step is then cyclized by heating in the presence of excess polyphosphoric acid, which not only serves as the agent responsible for causing cyclization but also serves as solvent for the reaction, or by other Friedel-Crafts type catalysts and non-aqueous solvents as suggested by G. A. Olah, "Friedel Crafts and Related Reactions", Vol. I Interscience Publishers, New York, 1963. The resulting 6,7-dimethoxy-2-methyl-4-oxo-1,2,3,4-tetrahydroquinoline (4) reaction containing mixture may then be poured into ice, extracted with chloroform and recovered by concentrating the combined dried organic extracts under reduced pressure.

The product of the fourth reaction step may then be acylated with an alkyl, phenyl or benzyl chloroformates in conventional fashion. The desired alkyl, phenyl or benzyl, 6,7-dimethoxy-2-methyl-4-oxo-1,2,3,4-tetrahydroquinoline-1-carboxylate (5) is then recovered from the reaction mixture via extraction, drying of the combined extract layers and concentration under reduced pressure.

Transformation of 5 into the useful intermediates of the present invention of structure 6 is effected by treatment of the appropriate alkyl, phenyl or benzyl 6,7-dimethoxy-2-methyl-4-oxo-1,2,3,4-tetrahydroquinoline-1-carboxylate with ethyl formate and sodium ethoxide in a solvent such as benzene. On completion of the reaction, which requires 2–6 hours at room temperature, the mixture is quenched in water. The product 6 remains in the water layer as the sodium salt and is liberated by neutralization with acid. The resulting product, which is isolated by extraction or decentation, is further purified by recrystallization from an appropriate solvent.

Synthesis for the racemic analgesic agents of structure 7 is effected through the reaction of 6 with the requisite amine. Experimentally, essentially equimolar amounts of the reactants are employed, plus as much as a ten-fold excess of amine in the case where $R_1$ and $R_2$ = H, in a suitable solvent such as benzene or ethanol. In instances where a volitile amine is used as the reactant room temperature reaction temperatures are employed with a corresponding reaction time of 12–28 hours. When the amine is higher boiling or if ammonium acetate is employed the reflux temperature of benzene or ethanol is the reaction temperature, shorter reaction times of 15–60 minutes being required.

The products of the final synthetic reaction are isolated by removal of the solvent and crystallization of the residue from some appropriate solvent. In instances where the final product is slightly contaminated with the starting reagent 6 the residue is partitioned between dilute base and a water immiscible solvent such as chloroform; the base solubilizing the starting material and the product being taken up in the non-aqueous solvent. The residual product, remaining after the non-aqueous solvent is removed, is purified by conventional means.

A further aspect of the present invention is the analgesic agent of structure 7 wherein $R_1$ and $R_2$ are hydrogen and $R_3$ is ethyl and wherein it is the d(+) enantiomer, or dextrorotatory enantiomer.

A particularly convenient method for preparing this compound is illustrated as follows:

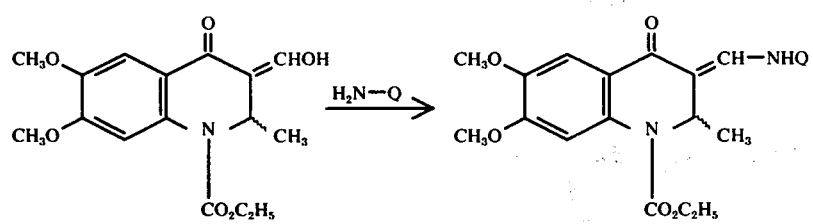

6(R₃ = C₂H₅);       7(R₃ = C₂H₅; R2 = Q)
mixture of diasteriomers

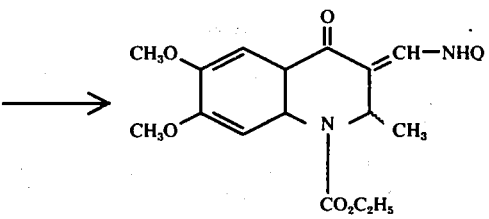

single diasteriomer single diasteriomer

7

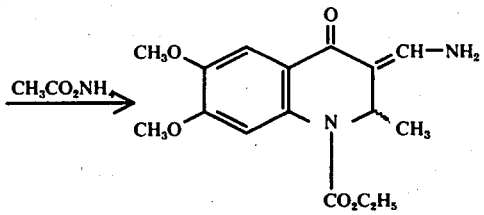

d(+) single optical isomer

In the first step of the above-depicted scheme, the hydroxymethylene compound of formula 6 is treated with one of the optical isomers of an amine of the formula NH₂Q which has a resolved asymmetric center in the group Q. This reaction produces a compound of the formula 7, as a mixture of two distereomers. These diastereomers are then separated in conventional fashion, e.g. by fractional crystallization or by chromatography. A wide variety of amines of the formula NH₂Q can be used, and one skilled in the art will realize that a particular amine will be chosen so that it affords the widest possible difference in physical properties, i.e. solubility and/or polarity, in the two diastereomers of the formula 7. For the purposes of the present invention, 1-(1-naphthyl)ethylamine is a particularly convenient amine. As has previously been discussed, the reaction of the hydroxymethylene compound of the formula 6 with the amine of the formula NH₂Q is usually carried out by contacting equimolar amounts of the two reagents in a reaction-inert organic solvent such as benzene, at about ambient temperature, for several hours, e.g. overnight. Removal of the solvent by evaporation then affords the product.

After separation into the two single diastereomers, each diastereomer of the formula 7 is then treated with ammonium acetate. This reaction, which is normally conducted using a large excess of ammonium acetate in a refluxing solvent such as ethanol, for several hours, brings about an amine exchange, and produces the compound of the formula 7 wherein R₁ and R₂ =H and R₃ =C₂H₅ in the dextrorotatory and levorotatory enantiomers All the starting reagents for these aforementioned synthetic reactions are either commercial reagents, or can be synthesized by literature procedures familiar to one skilled in the art.

As has been previously mentioned, the 3-aminomethylene compounds of the present invention wherein R₂ is dimethylaminoalkylene can form acid addition salts. Said basic compounds are converted to their acid addition salts by interaction of the base with an acid either in an aqueous or nonaqueous medium. In a similar manner, treatment of the acid addition salts with an equivalent amount of an aqueous base solution, e.g. alkali metal hydroxides, alkali metal carbonates and alkali metal bicarbonates or with an equivalent amount of a metal cation which forms an insoluble precipitate with the acid anion, results in the regeneration of the free base form. The bases thus regenerated may be reconverted to the same or a different acid addition salt.

In the utilization of the chemotherapeutic activity of those compounds of the present invention wherein R₂ is dimethylaminoalkylene, it is preferred, of course, to use pharmaceutically acceptable salts. Although water-insolubility, high toxicity, or lack of crystalline nature may make some particular salt species unsuitable or less desirable for use as such in a given pharmaceutical application, the water insoluble or toxic salts can be converted to the corresponding pharmaceutically acceptable bases by decomposition of the salt as described above, or alternately, they can be converted to any desired pharmaceutically acceptable acid addition salt.

Examples of acids which provide pharmaceutically acceptable anions are hydrochloric, hydrobromic, hydroiodic, nitric, sulfuric, or sulfurous, phosphoric, acetic, lactic, citric, tartaric, succinic, maleic and gluconic acids.

In the present invention, the racemic 3-aminomethylene compounds of structure 7 show analgesic activity. Outstanding for this therapeutic utility are 3-aminomethylene-6,7-dimethoxy-2-methyl-4-oxo-1,2,3,4-tetrahydro-1-quinoline carboxylic acid, ethyl ester, 3-benzylaminomethylene-6,7-dimethoxy-2-methyl-4-oxo-1,2,3,4-tetrahydro-1-quinoline carboxylic acid, ethyl ester, 3-methoxyethylaminomethylene-6,7-dimethoxy-2-methyl-4-oxo-1,2,3,4-tetrahydro-1-quinoline carboxylic acid, ethyl ester, 3-methylaminomethylene-6,7-dimethoxy-2-methyl-4-oxo-1,2,3,4-tetrahydro-1-quinoline carboxylic acid, ethyl ester, 3-aminomethylene-6,7-dimethoxy-2-methyl-4-oxo-1,2,3,4-tetrahydro-1-quinoline carboxylic acid, benzyl ester and 3-dimethylaminomethylene-6,7-dimethoxy-2-methyl-4-oxo-1,2,3,4-tetrahydro-1-quinoline carboxylic acid, ethyl ester.

When the dextrorotatory and levorotatory enantiomers of 3-aminomethylene-6,7-dimethoxy-2-methyl-4-oxo-1,2,3,4-tetrahydro-1-quinoline carboxylic acid, ethyl ester were prepared and tested for analgesic activity it was determined that while the dextrorotatory enantiomer shows analgesic activity, the levorotatory enantiomer does not demonstrate this utility. In addition to their usefulness as analgesic agents, the 3-aminomethylene compounds of the present invention are also central nervous system agents having tranquilizing activity.

Of those racemic 3-hydroxymethylene compounds (6) which are useful as intermediates, those which are particularly preferred for this use are 3-hydroxymethylene-6,7-dimethoxy-2-methyl-4-oxo-1,2,3,4-tetrahydro-1-quinoline carboxylic acid, ethyl ester and 3-hydroxymethylene-6,7-dimethoxy-2-methyl-4-oxo-1,2,3,4-tetrahydro-1-quinoline carboxylic acid, benzyl ester.

The analgesic agents of the present invention are characterized by relief of pain in humans. Standard procedures of detecting and comparing analgesic activity of compound in this series and for which there is an excellent correlation with human efficacy is the flinch-jump in rats test, as taught by W. Evans, *Psychopharmacologia*, 2, 318 (1961) and by S. Tenen, *Psychopharmacologia*, 12, 278 (1968).

The 3-aminomethylene compounds, useful as analgesics, can be administered either as individual therapeutic agents or as mixtures of therapeutic agents. They may be administered alone, but are generally administered with a pharmaceutical carrier selected on the basis of the chosen route of administration and standard pharmaceutical practice. For example, they can be administered orally in the form of tablets or capsules containing such excipients as starch, milk sugar, or certain types of clay, etc. They can be administered in the form of elixirs or oral suspensions with the active ingredients combined with emulsifying and/or suspending agents. They may be injected parenterally, and for this use they, or appropriate derivatives, may be prepared in the form of sterile aqueous solutions. Such aqueous solutions should be suitably buffered, if necessary, and should contain other solutes such as saline or glucose to render them isotonic.

Although the use of the present invention is directed toward the treatment of mammals in general, the preferred subject is humans. In determining an efficacious dose for human therapy, results of animal testing are frequently extrapolated and a correlation is assumed between animal test behavior and proposed human dosage. When a commercially employed standard is available, the dose level of the clinical candidate in humans is frequently determined by comparison of its performance with the standard in an animal test. For example, if a standard analgesic agent is administered effectively to humans at the rate of 100 to 400 mg. daily, it is assumed, then, that if compounds of the present invention have activity comparable to this standard in the test assay, that similar doses will provide comparable responses in humans.

Obviously, the physician will ultimately determine the dosage which will be most suitable for a particular individual, and it will vary with age, weight and response of the particular patient, as well as with the nature and extend of the symptoms and the pharmacodynamic characteristics of the particular agent to be administered. Generally, small doses will be administered initially, with a gradual increase in the dosage until the optimum level is determined. It will often be found that when the composition is administered orally, larger quantities of the active ingredient will be required to produce the same level as produced by a smaller quantity administered parenterally.

Having full regard for the foregoing factors, it is considered that a daily dosage of the compounds of the instant invention in humans of approximately 50 to 1500 mg., with a preferred range of 50 to 500 mg., will relieve pain effectively. These values are illustrative, and there may, of course, be individual cases where higher or lower dose ranges are merited.

The following examples are provided solely for the purpose of illustration and are not to be construed as limitations of this invention, many variations of which are possible without departing from the spirit or scope thereof.

EXAMPLE I

3-Aminomethylene-6,7-dimethoxy-2-methyl-4-oxo-1,2,3,4-tetrahydro-1-quinoline carboxylic acid, ethyl ester A. Ethyl-3-[(3,4-Dimethoxy)Anilino]-2-Butenoate 4-Aminoveratrole (62.0 g.), ethyl acetoacetate (63.0 g.), benzene (375 ml.), and acetic acid (2.1 ml.) are combined and refluxed in a flask equipped with a Dean-Stark strap to remove water until thin layer chromatography indicated the reaction is complete. The solvent is removed under reduced pressure to give a dark oil which crystallized upon standing. Recrystallization from hexane gives 79.0 g. of a tan powder, m.p. 59°–60°; a second drop afforded 6.7 g., m.p. 54°–56°. A sample is recrystallized from ethanol/water to give an analytical sample, m.p. 57°–58°.

Anal. Calc'd. for $C_{14}H_{19}NO_4$: C, 63.38; H, 7.22; N, 5.28 Found: C, 63.45; H, 7.06; N, 5.33.

B. Ethyl-3-[(3,4-Dimethoxy)Anilino]Butanoate

A mixture of 30.0 g. of the product of Example 1-A (m.p. 59°–60°), and 2.0 g. of platinum oxide in 250 ml. of acetic acid is hydrogenated in a Paar shaker at 50 p.s.i.; reduction is complete in 1 hr. The mixture is filtered and concentrated under reduced pressure to give an amber oil which is dissolved in chloroform and washed with sodium bicarbonate solution and saturated sodium chloride. The organic layer is dried over magnesium sulfate and concentrated under reduced pressure to give 30.0 g. of an amber oil which is used in the next step without further purification. A sample of oil is converted to the hydrochloride salt, m.p. 137.5°–139°. An equivalent sample of the hydrochloride salt (m.p. 138°–139.5°) is analyzed.

Anal. Calc'd. for $C_{14}H_{21}NO_4 \cdot HCl$ C, 55.35; H, 7.30; N, 4.61. Found: C, 55.73; H, 7.33; N, 4.33.

C. 3-[(3,4-Dimethoxy)Anilino]-Butanoic Acid

A 54 g. sample of the unpurified ester product of Example 1-B is combined with 17.5 g. of sodium hydroxide, 550 ml. of methanol and 130 ml. of water, and refluxed for 1.5 hrs. The reaction mixture is cooled, concentrated under reduced pressure, diluted with water and neutralized with 6N hydrochloric acid to give an oily mixture which is extracted with chloroform. The combined organic extracts are dried over anhydrous magnesium sulfate and concentrated under reduced pressure to give 48 g. of an oily product. This material is used in the next step without further purification.

D. 6,7-Dimethoxy-2-Methyl-4-Oxo-1,2,3,4-tetrahydroquinoline

The crude acid of Example I-C (48 g.) and 500 g. of polyphosphoric acid are heated for 1 hr. on a steam bath with vigorous stirring, then poured onto 700 g. of ice and extracted with chloroform. The organic extracts are dried over anhydrous magnesium sulfate and concentrated under reduced pressure to give 26.4 g. of a yellow solid, m.p. 145°–48° . A small sample is sublimed at 110° (.05 mm) to give a pale yellow solid, m.p. 150°–151°.

Anal. Calc'd. for $C_{12}H_{15}O_3N$: C, 65.14; H, 6.83; N, 6.33 Found: C, 65.18; H, 6.86; N, 6.25

E. Ethyl 6,7-Dimethoxy-2-Methyl-4-Oxo-1,2,3,4-tetrahydroquinoline-1-Carboxylate

A mixture of 15 g. of the quinoline product of Example I-D, 95 g. of potassium carbonate, and 225 ml. of methylene chloride are stirred for 1 hr., then 14.7 g. of ethyl chloroformate in 20 ml. of methylene chloride is added dropwise and the suspension is allowed to stir for 72 hrs. at room temperature. Additional 7.3 g. portions of ethyl chloroformate are added after 24 and 48 hrs. and 47 g. of potassium carbonate is added after 48 hrs. The reaction mixture is quenched with water and extracted several times with methylene chloride. The combined organic extracts are washed with water, dried over magnesium sulfate and concentrated under reduced pressure to give an oil which solidifies upon standing; trituration with 5% ethyl acetate in hexane gives 17 g. of a solid, m.p. 112°–116°. This solid is chromatographed on Silica Gel, eluting with 1:1 ethyl acetate/hexane, and recrystallized from 1:1 ethyl acetate/hexane to give 13.9 g. of white crystals, m.p. 116.5°–18°.

Anal. Cac'd. for $C_{15}H_{19}NO_5$: C, 61.42; H, 6.53; N, 4.78. Found: C, 61.37; H, 6.51; N, 4.78.

F. 3-Hydroxymethylene-6,7-dimethoxy-2-methyl-4-oxo-1,2,3,4-tetrahydro-1-quinoline carboxylic acid, ethyl ester To sodium ethoxide freshly prepared from 4.8 g. of sodium hydride and 6.0 ml. of ethanol is added 14.7 g. of ethyl 6,7-dimethoxy-2-methyl-4-oxo-1,2,3,4-tetrahydroquinoline-1-carboxylate and 19.8 ml. of ethyl formate in 150 ml. of benzene over a 45 min. period. The reaction mixture, after stirring at room temperature for 3 hrs., is poured onto 250 ml. of ice water. The aqueous layer is retained and the organic layer extracted with 1N aqueous sodium hydroxide. The base extracted is combined with the separated aqueous and backwashed with benzene. The aqueous layer is then added to 250 ml. of 12N hydrochloric acid, resulting in the formation of a yellow oil. Crystallization of the oil from hexane gives 15.4 g. of the desired intermediate, m.p. 98°–101° C. Further recrystallization from the same solvent raises the melting point to 129°–130° C.

Anal. Calc'd. for $C_{16}H_{19}O_6N$: C, 59.8; H, 6.0; N, 4.4. Found: C, 59.7; H, 5.9; N, 4.3.

G. 3-Aminomethylene-6,7-dimethoxy-2-methyl-4-oxo-1,2,3,4-tetrahydro-1-quinoline carboxylic acid, ethyl ester A reaction mixture comprising 58.5 g. of 3-hydroxymethylene-6,7-dimethoxy-2-methyl-4-oxo-1,2,3,4-tetrahydro-1-quinoline carboxylic acid, ethyl ester and 58.5 g. of ammonium acetate in 730 ml. of ethanol is heated to reflux for 10 min. The mixture is cooled to 40° C. and concentrated to a yellow solid. Th residue is taken up in 800 ml. of chloroform which is subsequently washed successively with water (1 × 450 ml.), 1N aqueous sodium hydroxide (2 × 450 ml.) and a brine solution (1 × 450 ml.). The chloroform layer is separated, dried over magnesium sulfate and concentrated to a yellow solid, 87.0 g., m.p. 86°–150° C. The crude product is further purified by recrystallization from ethyl acetate-hexane, 43.3 g., m.p. 160°–161° C.

Anal. Calc'd. for $C_{16}H_{20}O_5N_2$: C, 60.0; H, 6.3; H, 8.8. Found: C, 59.8; H, 6.2; N, 8.6.

EXAMPLE 2

3-Methylaminomethylene-6,7-dimethoxy-2-methyl-4-oxo-1,2,3,4-tetrahydro-1-quinoline carboxylic acid, ethyl ester A solution of 3.2 g. of 3-hydroxmethylene-6,7-dimethoxy-2-methyl-4-oxo-1,2,3,4-tetrahydro-1-quinoline carboxylic acid, ethyl ester and 2 g. of methylamine in 30 ml. of benzene is allowed to stir at room temperature overnight. The reaction mixture is concentrated to a foam which is subsequently crystallized twice from ethyl acetate-hexane, 1.95 g., m.p. 154°–156° C. A small sample is again recrystallized from the same solvent system for analysis, m.p. 155°–156° C.

Anal. Calc'd. for $C_{17}H_{22}O_5N_2$: C, 61.1; H, 6.6; N, 8.4. Found: C, 61.2; H, 6.6; N, 8.3.

EXAMPLE 3

3-Isopropylaminomethylene-6,7-dimethoxy-2-methyl-4-oxo-1,2,3,4-tetrahydro-1-quinoline carboxylic acid, ethyl ester A solution of 3.2 g. of 3-hydroxymethylene-6,7-dimethoxy-2-methyl-4-oxo-1,2,3,4-tetrahydro-1-quinoline carboxylic acid, ethyl ester in 30 ml. of benzene containing 650 mg. of isopropylamine is allowed to stir at room temperature for 48 hrs. The reaction solution is concentrated to give 4 g. of a yellow foam which could not be induced to crystallize.

Ultraviolet absorption peaks: $\lambda$max (m$\mu$) 258, 277 and 377.

EXAMPLE 4

Employing the procedure of Examples 1-E, 2 and 3 and starting with 3-hydroxymethylene-6,7-dimethoxy- 2-methyl-4-oxo-1,2,3,4-tetrahydro-1-quinoline carboxylic acid ethyl ester and the appropriate amine, the following compounds are synthesized:

3-ethylaminomethylene-6,7-dimethoxy-2-methyl-4-oxo-1,2,3,4-tetrahydro-1-quinoline carboxylic acid, ethyl ester; n-propylaminomethylene-6,7-dimethoxy-2-methyl-4-oxo-1,2,3,4-tetrahydro-1-quinoline carboxylic acid, ethyl ester; n-butylaminomethylene-6,7-dimethoxy-2-methyl-4-oxo-1,2,3,4-tetrahydro-1-quinoline carboxylic acid, ethyl ester; s-butylaminomethylene-6,7-dimethoxy-2-methyl-4-oxo-1,2,3,4-tetrahydro-1-carboxylic acid, ethyl ester; t-butylaminomethylene-6,7-dimethoxy-2-methyl-4-oxo-1,2,3,4-tetrahydro-1-quinoline carboxylic acid, ethyl ester; n-amylaminomethylene-6,7-dimethoxy-2-methyl-4-oxo-1,2,3,4-tetrahydro-1-quinoline carboxylic acid, ethyl ester; s-amylaminomethylene-6,7-dimethoxy-2-methyl-4-oxo-1,2,3,4-tetrahydro-1-quinoline carboxylic acid, ethyl ester; and t-amylaminomethylene-6,7-dimethoxy-2-methyl-4-oxo-1,2,3,4-tetrahydro-1-quinoline carboxylic acid, ethyl ester.

EXAMPLE 5

3-Propargylaminomethylene-6,7-dimethoxy-2-methyl-4-oxo-1,2,3,4-tetrahydro-1-quinoline carboxylic acid, ethyl ester To 1.6 g. of 3-hydroxymethylene-6,7-dimethoxy-2-methyl-4-oxo-1,2,3,4-tetrahydro-1-quinoline carboxylic acid, ethyl ester in 15 ml. of benzene is added 275 mg. of proparglyamine, and the resulting solution allowed to stir overnight at room temperature. The reaction mixture is concentrated in vacuo to about 2 g. and is then dissolved in 50 ml. of chloroform. The resulting solution is washed with 50 ml. of a 1N aqueous sodium hydroxide solution and subsequently dried over magnesium sulfate. Removal of the chloroform solvent leaves 1.9 g. of the desired product as a yellow foam.

Ultraviolet absorption peaks: $\lambda max(m\mu)$ 258, 278 and 374.

EXAMPLE 6

3-Phenylaminomethylene-6,7-dimethoxy-2-methyl-4-oxo-1,2,3,4-tetrahydro-1-quinoline carboxylic acid, ethyl ester Starting with 3.2 g. of 3-hydroxymethylene-6,7-dimethoxy-2-methyl-4-oxo-1,2,3,4-tetrahydro-1-quinoline carboxylic acid ethyl ester and 1.0 g. an aniline in 30 ml. of benzene and employing the reaction procedures of Example 5 provides 3.2 g. of the desired product as a yellow oil.

Ultraviolet absorption peaks $\lambda max(m\mu)$ 242, 363 287 and 403.

EXAMPLE 7

The procedure of Example 6 is repeated starting with the requisite amine and 3-hydroxymethylene-6,7-dimethoxy-2-methyl-4-oxo-1,2,3,4-tetrahydro-1-quinoline carboxylic acid ethyl ester, to provide the following compounds:

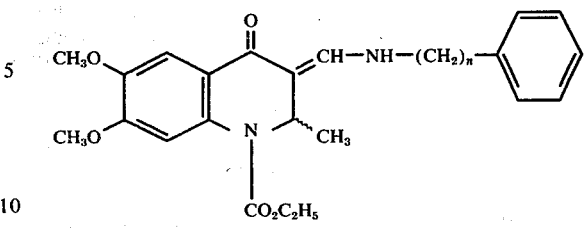

| | | Analysis | | | | | |
|---|---|---|---|---|---|---|---|
| | | Calc'd. | | | Found | | |
| n | m.p., ° C. | C | H | N | C | H | N |
| 1 | 115–116 | 67.3 | 6.4 | 6.8 | 67.4 | 6.4 | 6.8 |
| 2 | 122–123 | 67.9 | 6.7 | 6.6 | 67.7 | 6.6 | 6.3 |
| 3 | * | | | | | | |
| 4 | + | | | | | | |

*yellow oil; ultraviolet absorption peaks: $\lambda max(m\mu)$ 258, 277 and 376.
+yellow oil; ultraviolet absorption peaks: $\lambda max(m\mu)$ 256, 278 and 376.

EXAMPLE 8

The procedure of Example 6 is again repeated employing as starting reagents 3-hydroxymethylene-6,7-dimethoxy-2-methyl-4-oxo-1,2,3,4-tetrahydro-1-quinoline carboxylic acid, ethyl ester and the appropriate amine, to provide the following compounds:

3-($\alpha$-napthylaminomethylene)-6,7-dimethoxy-2-methyl-4-oxo-1,2,3,4-tetrahydro-1-quinoline carboxylic acid, ethyl ester; 3-($\beta$-naphthylaminomethylene)-6,7-dimethoxy-2-methyl-4-oxo-1,2,3,4-tetrahydro-1-quinoline carboxylic acid, ethyl ester; 3-($\alpha$-naphthylmethylaminomethylene)-6,7-dimethoxy-2-methyl-4-oxo-1,2,3,4-tetrahydro-1-quinoline carboxylic acid, ethyl ester; 3-($\beta$-naphthylethylaminomethylene)-6,7-dimethoxy-2-methyl-4-oxo-1,2,3,4-tetrahydro-1-quinoline carboxylic acid, ethyl ester; 3-($\alpha$-naphthylpropylaminomethylene)-6,7-dimethoxy-2-methyl-4-oxo-1,2,3,4-tetrahydro-1-quinoline carboxylic acid, ethyl ester; and 3-($\beta$-naphthylbutylaminomethylene)-6,7-dimethoxy-2-methyl-4-oxo-1,2,3,4-tetrahydro-1-quinoline carboxylic acid, ethyl ester.

EXAMPLE 9

3-Dimethylaminoethylaminomethylene-6,7-dimethoxy-2-methyl-4-oxo-1,2,3,4-tetrahydro-1-quinoline carboxylic acid, ethyl ester hydrochloride A benzene solution (30 ml.) containing 3.2 g. of 3-hydroxymethylene-6,7-dimethoxy-2-methyl-4-oxo-1,2,3,4-tetrahydro-1-quinoline carboxylic acid, ethyl ester and 1.0 g. of dimethylaminoethylamine is allowed to stir at room temperature for 18 hrs. The reaction solution is concentrated under reduced pressure to give 4.0 g. of a yellow oil. An ether solution of the base on treatment with hydrogen chloride gives the hydrochloride salt as a hydroscopic solid.

Ultraviolet absorption peaks: $\lambda max(m\mu)$ 258, 278 and 374.

EXAMPLE 10

3-Dimethylaminopropylaminomethylene-6,7-dimethoxy-2-methyl-4-oxo-1,2,3,4-tetrahydro-1-quinoline carboxylic acid, ethyl ester hydrochloride In a manner similar to Example 9, 3.2 g. of 3-hydroxymethylene-6,7-dimethoxy-2-methyl-4-oxo-1,2,3,4-tetrahydro-1-quinoline carboxylic acid, ethyl ester and 1.1 g. of 3-dimethylaminopropylamine in 30 ml. of benzene gives 4.8 g. of the product as a yellow oil. Treatment of an ethyl acetate solution of the free base with a 1N ethyl acetate hydrogen chloride solution provides the hydrochloride salt as a hydroscopic solid.

Ultraviolet absorption peaks λmax(mμ) 258, 277 and 375.

EXAMPLE 11

By substitution of 1.2 g. of 4-dimethylaminobutylamine for 1.1 g. of 3-dimethylaminopropylamine in Example 10, there is obtained on work-up 3.6 g. of 3-dimethylaminobutylamino-6,7-dimethoxy-2-methyl-4-oxo-1,2,3,4-tetrahydro-1-quinoline carboxylic acid, ethyl ester hydrochloride.

Ultraviolet absorption peaks: γmax(mμ) 258, 277 and 376.

The free base (470 mg.) generated by treating an aqueous solution of the hydrochloride salt with 1N sodium hydroxide solution followed by extraction with chloroform, is dissolved in 5 ml. of ethanol and treated with 127 mg. of maleic acid. The resulting suspension is warmed briefly in a steam bath to effect a solution, and is then treated with sufficient hexane to make the solution turbid. The product is allowed to crystallize giving 490 mg. of 3-dimethylaminobutylaminomethylene-6,7-dimethoxy-2-methyl-4-oxo-1,2,3,4-tetrahydro-1-quinoline carboxylic acid, ethyl ester maleate, m.p. 155°–160° C.

Anal. Calc'd. for $C_{26}H_{37}O_9N_3$: C, 58.3; H, 7.0; N, 7.9. Found: C, 58.1; H, 6.9; N, 7.8.

EXAMPLE 12

To 1.54 g. of 3-hydroxymethylene-6,7-dimethoxy-2-methyl-4-oxo-1,2,3,4-tetrhydro-1-quinoline carboxylic acid ethyl ester in 15 ml. of benzene is added 384 mg. of pyrrolidine, and the resulting yellow solution allowed to stir at room temperature for 18 hrs. The reaction mixture is concentrated in vacuo to a foam which is crystallized several times from ethyl acetate hexane to give 1.1 g. of 3-pyrrolidinomethylene-6,7-dimethoxy-2-methyl-4-oxo-1,2,3,4-tetrahydro-1-quinoline carboxylic acid, ethyl ester, m.p. 155°–156° C.

Anal. Calc'd. for $C_{20}H_{26}O_5N_2$: C, 64.2; H, 7.0; N, 7.5. Found: C, 64.2; H, 7.1; N, 7.4.

By employing the same procedure but substituting morpholine or piperidine for pyrrolidine there is obtained 3-morpholinomethylene-6,7-dimethoxy-2-methyl-4-oxo-1,2,3,4-tetrahydro-1-quinoline carboxylic acid, ethyl ester and 3-piperidinomethylene-6,7-dimethoxy-2-methyl-4-oxo-1,2,3,4-tetrahydro-1-quinoline carboxylic acid, ethyl ester, respectively.

EXAMPLE 13

3-Phenoxyethylaminomethylene-6,7-dimethoxy-2-methyl-4-oxo-1,2,3,4-tetrahydro-1-quinoline carboxylic acid, ethyl ester A solution of 1.6 g. of 3-hydroxymethylene-6,7-dimethoxy-2-methyl-4-oxo-1,2,3,4-tetrahydro-1-quinoline carboxylic acid, ethyl ester and 685 mg. of phenoxyethylamine in 15 ml. of benzene is allowed to stir overnight at room temperature. The reaction is concentrated to an oil and partitioned between 50 ml. of chloroform and 50 ml. of 1N aqueous sodium hdyroxide. The chloroform layer is separated, dried over magnesium sulfate and concentrated to give 1.9 g. of the desired product as a foam.

Ultraviolet absorption peaks: λmax(mμ) 259, 277 and 326.

EXAMPLE 14

3-methoxyethylaminomethylene-6,7-dimethoxy-2-methyl-4-oxo-1,2,3,4-tetrahydro-1-quinoline carboxylic acid, ethyl ester The procedure of Example 13 is repeated, starting with 3.21 g. of 3-hydroxymethylene-6,7-dimethoxy-2-methyl-4-oxo-1,2,3,4-tetrahydro-1-quinoline carboxylic acid, ethyl ester and 890 mg. of methoxyethylamine in 30 ml., to give 1.5 g. of the crude product as a yellow oil.

The oil is chromatographed on a column of silica gel (50 g.), eluting with a mixture of 50% ethanol/benzene. Fractions 6 thru 13 (12–13 ml. each) are combined and concentrated to dryness to give 1.0 g. of the pure product as a yellow oil.

EXAMPLE 15

3-Dimethylaminomethylene-6,7-dimethoxy-2-methyl-4-oxo-1,2,3,4-tetrahydro-1-quinoline carboxylic acid, ethyl ester Dimethylamine gas is bubbled into a solution of 3.2 g. of 3-hydroxymethylene-6,7-dimethoxy-2-methyl-4-oxo-1,2,3,4-tetrahydro-1-quinoline carboxylic acid, ethyl ester in 35 ml. of benzene and 50 ml. of tetrahydrofuran, and the reaction mixture stirred overnight at room temperature. The reaction mixture is concentrated in vacuo to dryness, and the residual product chromatographed on a silica gel column, using ethyl acetate-benzene (1:1; vol/vol) as the eluate. Fractions 6 thru 9 are combined and evaporated to dryness to give 600 mg. of the desired product. Recrystallization from ethyl acetate-pentane (2x) and ethyl acetate-hexane gave 180 mg. of pure product, m.p. 130°–131° C.

Anal. Calc'd. for $C_{18}H_{24}O_5N_2$: C, 62.1; H, 6.9; N, 8.0. Found: C, 61.6; H, 6.9; N, 7.9.

EXAMPLE 16

3-Hydroxymethylene-6,7-dimethoxy-2-methyl-4-oxo-1,2,3,4-tetrahydro-1-quinoline carboxylic acid, methyl ester A. Methyl 6,7-dimethoxy-2-methyl-4-oxo-1,2,3,4-tetradhydroquinoline-1-carboxylate A mixture of 1.2 g. (5.45 mmol) of the quinoline product of Example 1-D, 792 mg. (10.7 mmol) of dry pyridine and 5.5 ml. of methylene chloride are stirred and cooled by an ice-water bath while 758 mg. (8.02 mmol) of methyl chloroformate in 1 ml. of methylene chloride is added over a 10 min. period at a rate to maintain a 10°–15° C temperature. The ice bath is removed and the reaction allowed to stir at room temperature for 45 min. then poured onto 25 ml. of saturated sodium bicarbonate solution. The methylene chloride layer is separated and washed with 25 ml. saturated sodium bicarbonate solution and saturated sodium chloride solution, then dried over magnesium sulfate, and gravity filtered and evaporated to a yellow solid. The solid is triturated with 5 ml. anhydrous ether, filtered, and washed with minimum ether, then air dried to 1.1 g. of a yellow solid, m.p. 156°–158° C. This material is dissolved in 10 ml. of hot ethyl acetate, treated with 50 mg. Darco G60, filtered and crystallized by the addition of hexane to give 727 mg. of an off-white solid, m.p. 159°–160° C. after drying in vacuum at 100° C. (1mm) for 24 hrs.

Anal. Calc'd. for $C_{14}H_{17}O_5N$: C, 60.2; H, 6.1; N, 5.0 Found: C, 60.3; H, 6.3; N, 5.3

B. 3-Hydroxymethylene-6,7-dimethoxy-2-methyl-4-oxo-1,2,3,4-tetrahydro-1-quinoline carboxylic acid, methyl ester Methyl 6,7-dimethoxy-2-methyl-4-oxo-1,2,3,4-tetrahydroquinoline-1-carboxylate (13.8 g.) in 140 ml. of benzene containing 19 ml. of ethyl formate is added to sodium ethoxide freshly prepared from 4.8 g. of sodium hydride and 6 ml. of ethanol over a period of 45 min. After stirring at room temperature for 4 hrs. the reaction mixture is poured onto 250 ml. of ice-water. The aqueous layer is retained and the organic layer washed with 1N aqueous sodium hdyroxide. The washings are combined with the aqueous extracts and backwashed with benzene. The aqueous layer is then made acid with 12N hdyrochloric acid and extracted with chloroform. The organic phase is separated, dried over magnesium sulfate and evaporated in vacuo to dryness. The residue is employed in subsequent reactions without further purification.

EXAMPLE 17

3-Hydroxymethylene-6,7-dimethoxy-2-methyl-4-oxo-1,2,3,4-tetrahydro-1-quinoline carboxylic acid, butyl ester A. Butyl 6,7-dimethoxy-2-methyl-4-oxo-1,2,3,4-tetrahydroquinoline-1-carboxylate To a cooled mixture of 1.15 g. (5.17 mmol) of the quinoline product of Example 1-D, 751 mg. (10.15 mmol) of dry pyridine and 5.5 ml. of ethylene chloride stirred under a nitrogen atmosphere is added dropwise 1.03 g. (7.60 mmol) of butyl chloroformate in 1 ml. methylene chloride over 10 min. at a rate to maintain a 10°–15° C. temperature. After the addition is complete the bath is removed, the reaction stirred at room temperature for 45 min., and poured onto 25 ml. saturated sodium bicarbonate solution. The organic phase is collected and washed with 25 ml. of saturated sodium bicarbonate solution, 50 ml. saturated sodium chloride solution, dried over magnesium sulfate, then gravity filtered and evaporated to a viscous amber oil. Evaporative distillation at 110° C. (0.05 mm) gave 1.4 g. of a very viscous amber oil.

Anal. Calc'd. for $C_{17}H_{23}O_5N$: C, 63.5; H, 7.2; N, 4.4 Found: C, 63.7; H, 7.2; N, 4.1

B. 3-Hydroxmethylene-6,7-dimethoxy-2-methyl-4-oxo-1,2,3,4-tetrahydro-1-quinoline carboxylic acid, butyl ester To sodium ethoxide freshly prepared from 4.8 g. of sodium hydride and 6.0 ml. of ethanol is added 16.0 g. of butyl 6,7-dimethoxy-2-methyl-4-oxo-1,2,3,4-tetrahydroquinoline-1-carboxylate and 19.8 ml. of ethyl formate in 150 ml. of benzene over a 30 min. period. The reaction mixture, after stirring at room temperature for 4 hrs., is poured onto 250 ml. of ice-water. The aqueous layer is retained and the organic layer extracted with 1N aqueous sodium hydroxide. The base extracted is combined with the separated aqueous and backwashed with benzene. The aqueous layer is then added to 250 ml. of 12N hydrochloric acid. The resulting yellow oil is extracted with chloroform and the chloroform layer dried over magnesium sulfate. The solvent is removed under reduced pressure and the residual product used in subsequent reactions without further purification.

EXAMPLE 18

3-Hydroxymethylene-6,7-dimethoxy-2-methyl-4-oxo-1,2,3,4-tetrahydro-1-quinoline carboxylic acid, benzyl ester A. Benzyl 6,7-dimethoxy-2-methyl-4-oxo-1,2,3,4-tetrahydroquinoline-1-carboxylate To a solution of 10.0 g. (45.3 mmol) of the quinoline product of Example 1-D in 75 pyridine cooled to 0° C. is added over a 30 min. period 55 ml. of benyl chloroformate. After 20 min. the reaction mixture was warmed on a steam bath during which time the reaction became exothermic. Heating at steam bath temperatures is continued for 30 min., and the mixture allowed to cool to room temperature. The resulting suspension is added to a mixture of 550 ml. chloroform/300 ml. water. The chloroform layer is separated, washed successively with 10% hydrochloric acid (3 × 300 ml.), saturated aqueous sodium bicarbonate (1 × 200 ml.) and brine (1 × 200 ml.), and dried over magnesium sulfate. The chloroform layer is concentrated to dryness and the residue crystallized from ethyl acetane-hexane, 14.0 g. Recrystallization from the same solvent system gave 11.4 g. of the desired product, m.p. 127.5°–129.5° C.

B. 3Hydroxymethylene-6,7-dimethoxy-2-methyl-4-oxo-1,2,3,4-tetrahydro-1-quinoline carboxylic acid, benzyl ester Following the procedure of Examples 1-E, 16-B and 17-B, 9.5 g. of benzyl 6,7-dimethoxy-2-methyl-4-oxo-1,2,3,4-tetrahydroquinoline-1-carboxylate, 10.95 ml. of ethyl formate and sodium ethoxide prepared from 2.57 g. of sodium hydride and 3.23 ml. of ethanol in 120 ml. of benzene gave on work-up a yellow oil which on crystallization afforded 6.0 g. of crude product, m.p. 106°–110° C. The analytical same is recrystallized several times from methanol, m.p. 116°–118° C.

Anal. Calc'd. for $C_{21}H_{21}O_6N$: C, 65.8; H, 5.6; N, 3.7. Found: C, 65.4; H, 5.6; N, 3.7.

EXAMPLE 19

Starting with the appropriately substituted phenyl or benzyl chloroformate and 6,7-dimethoxy-2-methyl-4-oxo-1,2,3,4-quinoline and employing the procedure of Example 18-A and B, the following 3-hydroxymethylene-6,7-dimethoxy-2-methyl-4-oxo-1,2,3,4-tetrahydro-1-quinoline carboxylic acid, phenyl and benzyl esters are synthesized:

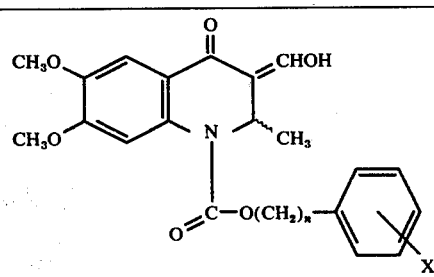

| n | X |
|---|---|
| 0 | 2-F |
| 0 | 4-F |
| 0 | 3-Cl |
| 0 | 4-Cl |
| 0 | 2-CH₃ |

-continued

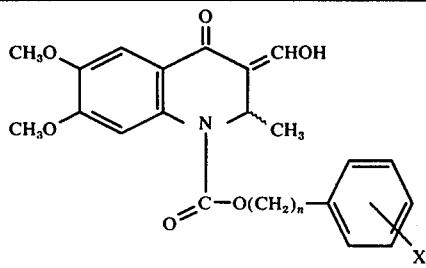

| n | X |
|---|---|
| 0 | 3-CH₃ |
| 0 | 4-CH₃ |
| 0 | 3-OCH₃ |
| 0 | 4-OCH₃ |
| 0 | 3-CF₃ |
| 1 | 2-F |
| 1 | 3-F |
| 1 | 4-F |
| 1 | 2-Cl |
| 1 | 4-Cl |
| 1 | 3-CH₃ |
| 1 | 4-CH₃ |
| 1 | 2-OCH₃ |
| 1 | 4-OCH₃ |
| 1 | 2-CF₃ |
| 1 | 4-CH₃ |

EXAMPLE 20

The procedure of Example 5 is repeated, starting with the appropriate amine and 3-hyroxymethylene-6,7-dimethoxy-2-methyl-4-oxo-1,2,3,4-tetrahydro-1-quinoline carboxylic acid, alkyl ester, to provide the following compounds:

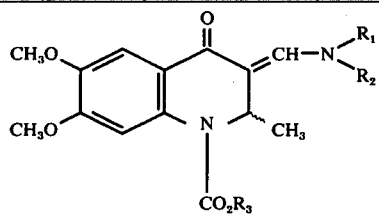

| R₁ | R₂ | R₃ |
|---|---|---|
| H— | C₂H₅— | CH₃— |
| H— | CH≡CCH₂— | CH₃— |
| CH₃— | CH₃— | CH₃— |
| CH₃— | C₆H₅ | CH₃— |
| CH₃— | C₆H₅O(CH₂)₂— | CH₃— |
| CH₃— | (CH₃)₂N(CH₂)₂— | CH₃— |
| CH₃— | CH₃(CH₂)₄— | C₂H₅— |
| CH₃ | CH₃O(CH₂)₂— | C₂H₅— |
| —(CH₂)₅— | | CH₃— |
| CH₃— | (CH₃)₂N(CH₂)₄— | C₂H₅— |
| CH₃— | α-C₁₀H₇(CH₂)₂— | C₂H₅— |
| CH₃— | C₆H₅(CH₂)₃— | C₂H₅— |
| CH₃— | i-C₃H₇ | C₂H₅— |
| CH₃— | C₆H₅— | C₂H₅— |
| H— | n-C₄H₉— | n-C₃H₇— |
| CH₃— | C₂H₅— | n-C₃H₇— |
| H— | C₆H₅(CH₂)₂— | n-C₃H₇— |
| H— | C₆H₅CH₂— | n-C₃H₇— |
| CH₃— | (CH₃)₂N(CH₂)₃— | n-C₃H₇— |
| H— | H— | i-C₃H₇— |
| —(CH₂)₅— | | i-C₃H₇— |
| H— | n-C₅H₁₁— | i-C₃H₇— |
| CH₃— | C₆H₅O(CH₂)₂— | i-C₃H₇— |
| H— | β-C₁₀H₇CH₂— | i-C₃H₇— |
| H— | H— | n-C₄H₉— |
| CH₃— | CH₃O(CH₂)₂— | n-C₄H₉— |
| —(CH₂)₄— | | n-C₄H₉— |
| CH₃— | C₆H₅(CH₂)₄— | n-C₄H₉— |
| H— | C₆H₅— | n-C₄H₉— |
| H— | CH≡CCH₂— | n-C₄H₉— |

-continued

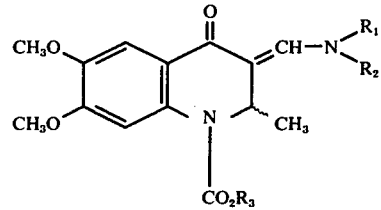

| R₁ | R₂ | R₃ |
|---|---|---|
| H— | H— | n-C₅H₁₁— |
| H— | α-C₁₀H₇— | n-C₅H₁₁— |
| CH₃— | CH≡CCH₂— | n-C₅H₁₁— |
| CH₃— | CH₃O(CH₂)₂— | n-C₅H₁₁— |
| H— | H— | i-C₅H₁₁— |
| CH₃— | H— | i-C₅H₁₁— |
| CH₃— | CH₃— | i-C₅H₁₁— |
| —(CH₂)₅— | | i-C₅H₁₁— |
| —(CH₂)₂O(CH₂)₂— | | i-C₅H₁₁— |

EXAMPLE 21

3-Aminomethylene-6,7-dimethoxy-2-methyl-4-oxo-1,2,3,4-tetrahydro-1-quinoline carboxylic acid, benzyl ester A mixture of 5.0 g. of 3-hydroxymethylene-6,7-dimethoxy-2-methyl-4-oxo-1,2,3,4-tetrahydro-1-quinoline carboxylic acid, benzyl ester and 5.0 g. of ammonium acetate in 200 ml. of ethanol is heated to reflux for 35 min. The reaction is concentrated to dryness and the residue taken up in 200 ml. of chloroform. The chloroform solution is then washed successively with water (1 × 100 ml.), 1N aqueous sodium hdyroxide (2 × 100 ml.) and brine (1 × 100 ml.), dried over magnesium sulfate and concentrated to dryness. The residual oil is crystallized from ethyl acetate, 3.34 g., m.p. 143°–149.5° C. and 1.3 g. recrystallized from the same solvent, 660 mg., m.p. 144°–146.5° C.

Anal. Calc'd. for $C_{21}H_{22}O_5N_2$: C, 66.0; H, 5.8; N, 7.3. Found: C, 65.9; H, 5.9; N, 7.3.

EXAMPLE 22

Starting with the appropriate 3-hyroxymethylene-6,7-dimethoxy-2-methyl-4-oxo-1,2,3,4-tetrahydro-1-quinoline carboxylic acid, phenyl or benzyl ester from Example 19 and the requisite amine, the following products are prepared:

| n | X | R₁ | R₂ |
|---|---|---|---|
| 0 | 2-F— | H— | CH₃— |
| 0 | 2-F— | CH₃— | C₂H₅— |
| 0 | 4-Cl— | H— | H— |
| 0 | 4-Cl— | H— | C₆H₅— |
| 0 | 2-CH₃— | H— | C₆H₅— |
| 0 | 2-CH₃— | H— | C₆H₅(CH₂)₂— |
| 0 | 4-CH₃— | H— | C₆H₅O(CH₂)₂— |
| 0 | 4-CH₃— | CH₃— | (CH₃)₂N(CH₂)₂— |
| 0 | 4-CH₃O— | CH₃— | CH₃O(CH₂)₂— |

-continued

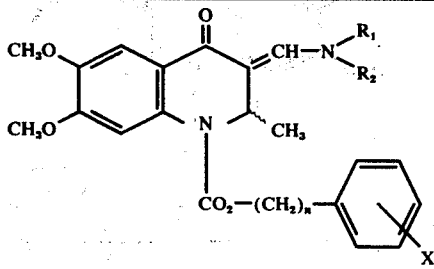

| n | X | R₁ | R₂ |
|---|---|---|---|
| 0 | 4-CH₃O— | H— | H— |
| 0 | 3-CH₃O— | H— | H— |
| 0 | 3-CH₃O— | H— | α-C₁₀H₇CH₂— |
| 0 | 4-F— | H— | CH≡CCH₂— |
| 0 | 4-F— | CH₃— | CH≡CCH₂— |
| 0 | 3-Cl— | —(CH₂)₅— | |
| 0 | 4-F— | —(CH₂)₂O(CH₂)₂— | |
| 0 | 3-CF₃— | —(CH₂)₄— | |
| 1 | 2-F— | H— | H— |
| 1 | 2-F— | CH₃— | CH₃(CH₂)₄— |
| 1 | 3-F— | —(CH₂)₅— | |
| 1 | 3-F— | CH₃— | CH₃O(CH₂)₂— |
| 1 | 4-F— | H— | H— |
| 1 | 4-F— | —(CH₂)₄— | |
| 1 | 2-Cl— | CH₃— | C₆H₅O(CH₂)₂— |
| 1 | 4-Cl— | CH₃— | C₆H₅(CH₂)₂— |
| 1 | 3-CH₃— | CH₃— | i-C₃H₇— |
| 1 | 3-CH₃— | H— | β-C₁₀H₇CH₂— |
| 1 | 4-CH₃— | CH₃— | C₂H₅— |
| 1 | 2-CH₃O— | CH₃— | (CH₃)₂N(CH₂)₂— |
| 1 | 4-CH₃O— | H— | CH≡CCH₂— |
| 1 | 4-CH₃O— | —(CH₂)₆— | |
| 1 | 2-CF₃— | —(CH₂)₂O(CH₂)₂— | |
| 1 | 4-CF₃— | CH₃— | C₂H₅— |

EXAMPLE 23 d(+)-3-Aminomethylene-6,7-dimethoxy-2-methyl-4-oxo-1,2,3,4-tetrahydro-1-quinoline carboxylic acid, ethyl ester A. d(+) and l(—) 3-[N-(1-{1-Naphthyl}ethyl)aminomethylene]-6,7-dimethoxy-2-methyl-4-oxo-1,2,3,4-tetrahydro-1-quinoline carboxylic acid, ethyl ester A mixture of 6.4 g. of racemic 3-hydroxymethylene-6,7-dimethoxy-2-methyl-4-oxo-1,2,3,4-tetrahydro-1-quinoline carboxylic acid, ethyl ester from Example 1-F and 3.2 g. of d-1-(1-napthyl)ethylamine in 60 ml. of benzene are stirred at ambient temperature for 16 hrs. The solvent is removed by evaporation in vacuo, and the residue is redissolved in 250 ml. of chloroform. The chloroform solution is washed with 150 ml. of 1N sodium hydroxide, and then the dried organic phase is concentrated to dryness in vacuo. This affords 9.3 g. of 3-[N-(1-[1-napthyl]ethyl)aminomethylene]-6,7-dimethoxy-2-methyl-4-oxo-1,2,3,4-tetrahydro-1-quinoline carboxylic acid, ethyl ester as a mixture of two diasteriomers, [α]D 25 = —364.17° (1% solution in CHCl₃).

A 2.0-g. aliquot of the above mixture of diasteriomers is dissolved in 30 ml. of chloroform and to the resultant solution of chromatographic grade silica gel. The chloroform is then removed by evaporation in vacuo, and the residue placed on top of a chromotographic column which has been prepared by placing 760 g. of silica gel in a 50 inch × 1.6 inch nylon tube. The column is eluted with 1,280 ml. of 15:1 benzene: acetonitrile, and then allowed to run dry. The column is cut into small pieces, approximately 1 inch long, and each piece is triturated with ethyl acetate. The silica gel is removed by filtration, and the ethyl acetate removed by evaporation in vacuo, giving 15 column fractions.

Fractions 1–5 are combined, giving 290 mg. of the more polar diasteriomer of the above diasteriomeric mixture. The diasteriomer has [α]D 25 = —247.1° (1% in CHCl₃).

Fractions 14 and 15 are combined, giving 250 mg. of the less polar diasteriomer of the above diasteriomeric mixture. It has [α]D 25 = —407.2° (1% in CHCl₃).

Fractions 6–13 are rechromotographed, to provide further quantities of each of the pure diasteriomers.

B. d(+)-3-Aminomethylene-6,7-dimethoxy-2-methyl-4-oxo-1,2,3,4-tetrahydro-1-quinoline carboxylic acid, ethyl ester To a solution of 2.06 g. of the polar diasteriomer, prepared by reaction of racemic 3-hydroxymethylene-6,7-dimethoxy-2-methyl-4-oxo-1,2,3,4-tetrahydro-1-quinoline carboxylic acid, ethyl ester with d-1-(1-naphthyl)-ethylamine (Example 23-A), in 40 ml. of ethanol, is added 50 g. of ammonium acetate, and the reaction mixture heated to reflux. After 20 min. reflux and after 45 min. reflux, additional 25-g. quantities of ammonium acetate are added. The reaction mixture is heated under reflux for a total of 6 hrs., and then cooled to 25° C. and poured into 1,000 ml. of ethyl acetate. The ethyl acetate solution is washed successively with water and sodium bicarbonate, dried over magnesium sulfate (MgSO₄), and concentrated in vacuo to give 1.55 g. of crude product as a viscous oil. The crude product is purified by column chromotography using silica gel as absorbant and 6:4 benzene-ethyl acetate as eluant, followed by recrystallization from chloroform-hexane, giving 440 mg. of material, m.p. 70°–120° C. A further recrystallization gave 290 mg., m.p. 92°–95° C., [α]D 25 = +97.62 (0.25% in CHCl₃).

Anal. Calc'd. for C₁₆H₂₀N₂O₅: C, 60.0; H, 6.3; N, 8.8 Found: C, 60.1; H, 6.5; N, 8.3.

A further 500 mg. of product m.p. 88°–90° C. is obtained from the recrystallization mother liquors, giving a total yield of 790 mg. (56%).

EXAMPLE 24

The 3-aminomethylene analgesics of the present invention are evaluated by the aforementioned Flinch Jump Test which is a modification of the Evans, *Psychopharmacologia*, 2, 318 (1961), flinch jump procedure and comprises measuring "pain thresolds." The procedure involves placing Sprague-Dawley rats weighing 210–270 g. in a chamber and presenting them with a series of 1 sec. foot shocks in increasing intensity of 0.1, 0.2, 0.3, 0.4, 0.6, 0.8; 1.2 etc. (in milliamps). The shocks are presented at 30 sec. intervals at 0.5, 2.0 and 4.0 hrs. after i.p. administration of the drug at a dose of 56 mg./kg., and the animal behavior is rated at the point at which the animals jump.

The following results are obtained when the performance of the d l or d forms of the indicated compounds are measured in the Flinch-Jump Test:

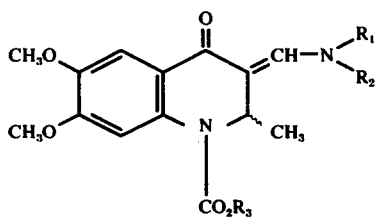

| Compound | Evaluation of Jump (ma)[1] | | |
|---|---|---|---|
| | 0.5 hr. | 2.0 hrs. | 4.0 hrs. |
| dl $R_1, R_2 = H; R_3 = C_2H_5-$ | 1.64 | 1.64 | 1.58 |
| dl $R_1, R_2 = H; R_3 = C_6H_5CH_2-$ | 1.47 | 2.37 | 1.80 |
| dl $R_1 = H; R_2 = CH_3; R_3 = C_2H_5-$ | 1.36 | 1.69 | — |
| dl $R_1 = CH_3; R_2 = CH_3; R_3 = C_2H_5$ | 1.41 | 1.10 | — |
| dl $R_1 = H; R_2 = i-C_3H_7; R_3 = C_2H_5$ | 1.31 | 1.25 | — |
| dl $R_1 = H; R_2 = C_6H_5CH_2; R_3 = C_2H_5$ | 1.58 | 1.41 | — |
| dl $R_1 = H; R_2 = CH\equiv CCH_2-; R_3 = C_2H_5$ | 1.26 | 1.31 | — |
| dl $R_1, R_2 = -(CH_2)_4-; R_3 = C_2H_5$ | 1.0 | 0.94 | — |
| dl $R_1 = H; R_2 = C_6H_5; R_3 = C_2H_5$ | .94 | 1.15 | — |
| dl $R_1 = H; R_2 = (CH_3)_2N(CH_2)_2-; R_3 = C_2H_5$ | 1.15 | 1.05 | — |
| dl $R_1 = H; R_2 = CH_3O(CH_2)_2-; R_3 = C_2H_5$ | 1.91 | 1.58 | — |
| d $R_1, R_2 = H; R_3 = C_2H_5$ | 1.53[3] | 1.42 | 1.15 |

-continued

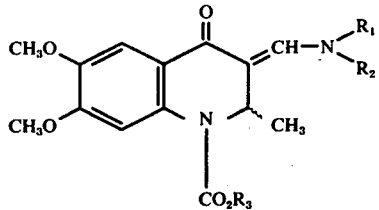

| Compound | Evaluation of Jump (ma)[1] | | |
|---|---|---|---|
| | 0.5 hr. | 2.0 hrs. | 4.0 hrs. |
| Codeine sulfate | 0.94 | 0.99 | 0.89 |

[1]milliamps
[2]times: 0.75 hr., 3.0 hrs. and 5.0 hrs.
[3]dose: 32 mg./kg.

What is claimed is:

1. A racemic compound selected from the group consisting of

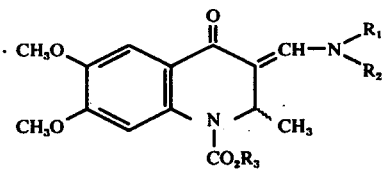

wherein $R_1$ and $R_2$ taken together with the nitrogen to which they are attached form a heterocyclic ring selected from the group consisting of piperidino, pyrrolidino, and morpholino and $R_3$ is selected from the group consisting of alkyl having from one to five carbon atoms, phenyl, benzyl and mono-substituted benzyl and phenyl wherein said substituent is selected from the group consisting of fluoro, chloro, methyl, methoxy and trifluoromethyl.

* * * * *